US010393711B2

(12) United States Patent
Nettesheim

(10) Patent No.: US 10,393,711 B2
(45) Date of Patent: Aug. 27, 2019

(54) SYSTEM AND METHOD FOR IDENTIFYING AND DISTINGUISHING MATERIALS, METHOD FOR IDENTIFYING OR DISTINGUISHING MATERIALS, AND MEASURING DEVICE FOR RECORDING MATERIAL PROPERTIES OF MATERIALS

(71) Applicant: Maschinenfabrik Reinhausen GmbH, Regensburg (DE)

(72) Inventor: Stefan Nettesheim, Berlin (DE)

(73) Assignee: Maschinenfabrik Reinhausen GmbH, Regensburg (DE)

( * ) Notice: Subject to any disclaimer, the term of this patent is extended or adjusted under 35 U.S.C. 154(b) by 1010 days.

(21) Appl. No.: 14/593,016

(22) Filed: Jan. 9, 2015

(65) Prior Publication Data
US 2015/0120213 A1 Apr. 30, 2015

Related U.S. Application Data

(63) Continuation of application No. PCT/EP2013/064513, filed on Jul. 9, 2013.

(30) Foreign Application Priority Data

Jul. 9, 2012 (DE) .................. 10 2012 106 132
Jul. 2, 2013 (DE) .................. 10 2013 106 915

(51) Int. Cl.
*G01N 27/04* (2006.01)
*G01N 33/00* (2006.01)
*G01N 35/00* (2006.01)

(52) U.S. Cl.
CPC ............. *G01N 33/00* (2013.01); *G01N 27/04* (2013.01); *G01N 35/00871* (2013.01);
(Continued)

(58) Field of Classification Search
CPC .. G01N 33/00; G01N 27/04; G01N 35/00871; G01N 2033/0091; G01N 2035/00653; G01N 2035/00881
See application file for complete search history.

(56) References Cited

U.S. PATENT DOCUMENTS 3,526,127 A 9/1970 Sarkis
5,074,158 A 12/1991 Tokoyama
(Continued)

FOREIGN PATENT DOCUMENTS

DE 3308998 9/1984
DE 69417519 11/1999
(Continued)

OTHER PUBLICATIONS

Anonymous: "Signatur (Programmierung)—Wikipedia", Dec. 18, 2013 (Dec. 18, 2013), XP055094055, retrieved from the Internet: URL:http://de.wikipedia.org/wiki/Signatur_(Programmierung) [retrieved on Dec. 18, 2013].

(Continued)

*Primary Examiner* — Mohamed Charioui
*Assistant Examiner* — Catherine T. Rastovski
(74) *Attorney, Agent, or Firm* — Simpson & Simpson, PLLC

(57) ABSTRACT

A system for identifying or distinguishing materials, comprising at least one local apparatus and a central station. Each local apparatus comprises at least one measuring device for recording at least one actual signature for materials each and at least one local computer communicatively connected to the at least one measuring device, the at least one local computer having a local database for storing and/or processing the actual signature. The at least one central station comprises a server having a central database for storing and/or processing the actual signatures of the (Continued)

local apparatus. Furthermore, the system comprises a network, which communicatively connects the local computers of the local units via the server of the center. The invention further relates to a corresponding method for operating a system, to an analysis method for identifying or distinguishing the materials, and to a measuring device for recording material properties of the materials.

20 Claims, 9 Drawing Sheets

(52) U.S. Cl.
CPC ............... *G01N 2033/0091* (2013.01); *G01N 2035/00653* (2013.01); *G01N 2035/00881* (2013.01)

(56) References Cited

U.S. PATENT DOCUMENTS

| | | |
|---|---|---|
| 2005/0063865 A1 | 3/2005 | Bonne et al. |
| 2006/0129345 A1 | 6/2006 | Parvin et al. |
| 2007/0192032 A1* | 8/2007 | David ................... A01M 1/026 702/19 |
| 2009/0261847 A1 | 10/2009 | Petrovsky et al. |
| 2009/0289448 A1* | 11/2009 | Sample ................. B01L 3/5457 283/67 |
| 2010/0209004 A1* | 8/2010 | Potuluri ................. G01N 21/31 382/209 |

FOREIGN PATENT DOCUMENTS

| | | |
|---|---|---|
| DE | 60023005 | 7/2006 |
| EP | 0606121 | 7/1994 |
| WO | WO1999/061902 | 12/1999 |

OTHER PUBLICATIONS

Anonymous: "Digitale Signatur—Wikipedia", Dec. 18, 2013 (Dec. 18, 2013), XP055094057, retrieved from the Internet: URL:http://de.wikipedia.org/wiki/Digitale_Signatur [retrieved on Dec. 18, 2013].
Anonymous: "Elektronische Signatur—Wikipedia", Dec. 18, 2013 (Dec. 18, 2013), XP055094058, retrieved from the Internet: URL:http://de.wikipedia.org/wiki/Elektronische_Signatur [retrieved on Dec. 18, 2013].
Anonymous: "Server (Computing)-Wikipedia, the free encyclopedia", Dec. 17, 2013 (Dec. 17, 2013), XP055094032, retrieved from the Interent: URL:http://en.wikipedia.org/wiki/Server_(computing) [retrieved on Dec. 17, 2013].

* cited by examiner

SYSTEM AND METHOD FOR IDENTIFYING AND DISTINGUISHING MATERIALS, METHOD FOR IDENTIFYING OR DISTINGUISHING MATERIALS, AND MEASURING DEVICE FOR RECORDING MATERIAL PROPERTIES OF MATERIALS

CROSS-REFERENCE TO RELATED APPLICATIONS

This application is filed under 35 U.S.C. § 120 and § 365(c) as a continuation of International Patent Application PCT/EP2013/064513, filed on Jul. 9, 2013, which application claims priority from German Patent Application No. 10 2012 106 132.7, on filed Jul. 9, 2012, and German Patent Application No. 10 2013 106 915.0, filed on Jul. 2, 2013, which applications are incorporated herein by reference in their entireties.

FIELD OF THE INVENTION

The invention relates to a system for identifying or distinguishing materials. Moreover, the invention relates to method for identifying or distinguishing materials by use of a system.

Additionally, the invention relates to a method for identifying or distinguishing materials.

Furthermore, the invention relates to a measuring device for determining material properties of materials.

BACKGROUND OF THE INVENTION

To analyze heterogeneous substances or mixtures of substances, such as powders, pastes, suspensions, or solids, a variety of different measurement methods are used, wherein each of which aims at one or more specific properties. A powder can be examined by light scattering studies in order to determine the particle size distribution. The chemical properties of a material can be determined with high accuracy both in volume and in the surface composition. Analogously, electrical and magnetic properties of the material or material mixture can be measured. The time consuming and equipment expense of these measurement methods are very different. However, not all of the methods are suitable for a sufficiently rapid or real-time process control.

Methods for analyzing powder and precise material analysis are usually complex, costly and time-consuming processes. Especially, with heterogeneous materials such as powders, pastes, suspensions, solids, heterogeneous mixtures, the correlation between physical and chemical properties and behavior during the manufacturing process is complex and difficult to analyze. Therefore, usually empirical knowledge is used. In general, it is not possible to conclude from the collective properties of a large particle number, such as a bulk material or a powder, the properties of individual particles, and vice versa.

Even with an accurate chemical analysis of a very large number of particles and a high-precision determination of particle size distribution and particle shapes, it is difficult to conclude about process relevant data, such as free-flowing properties, clumping tendency or the apparent density. The complexity of bulk material or powders complicates quality assurance in a production processes.

In industrially relevant processes, both the statistical distribution of particle sizes and particle shapes, as well as the chemical composition of the particles in the bulk and on the surface, is important. In powder mixtures, the degree of complexity is correspondingly higher.

For production, it may be necessary to accurately detect whether a change in the composition of the starting materials being fed through. Any change of the material batch, the material source, or the supplier increases the risk that established and empirically controlled processes become unstable. Often, supplier side changes of the material composition are not communicated since the change is considered to be of little relevance. Errors in the production process are often complex and subjected to a causal chain. Later on, one can therefore hardly prove that a certain defective raw material is the cause of an error.

The translation DE 600 23 005 T2 of the European patent EP 1 194 762 B1 discloses a system, apparatus and method for a multiple logging of a combination of both chemical and physical characteristics of a particular analyte in a given environment to generate a unique signature. In addition, an unknown analyte can be detected and identified by comparison of its unknown signature with a stored output signature of a known analyte or a mixture of substances. A measurement data set is evaluated by algorithms. The algorithm can optimize the feature selection and the sensor selection. The algorithm may be a neural network which is trained by correcting the wrong or undesirable outputs on the basis of predetermined criteria in a collection of data. Amongst others, related correlation variables are transformed into a smaller number of uncorrelated variables (principal component analysis, PCA). The aim of the PCA is to reduce the dimensionality of the data set. Applications include control of material quality, labor protection or monitoring of food and agricultural products. However, the method disclosed does not analyze the material in terms of macroscopic material properties, such as particle size, size distribution, state, rheological properties and mixing ratio of powdery and heterogeneous materials. Also, the disclosed automated material quality control is not operated continuously or integrated into existing production processes. Further, the signature of a substance is not to process- or machine-correlated.

The translation DE 694 17 519 T2 of the European patent application EP 0 606 121 B1 discloses a device for automatic quality inspection of selected metrics of powdery products. A variety of test equipment and data station computers capture these measurements parallel to subsets of the powder. Measurement values include the particle size, the bulk density or the degree of polymerization. The measurement data obtained are combined in a central data processing and compared with the quality standards. Also, impurities are determined and recorded quantitatively. The selection of the measured values, however, is not automated. There is no algorithm provided for determining a reduced or minimal set of measurement values that are sufficient for a unique sample determination. Furthermore, the material subsets to be measured are supplied in containers with robotic arms according to labels on the containers to an appropriate measuring device. Also, during the measurements and their evaluation, environmental conditions are not considered.

The German patent application DE 33 08 998 A1 discloses a device specially designed for the measurement of dispersive properties of powders or aerosols. Chemical parameters or values are not determined. Powders are no identified. A digital data acquisition and data analysis is not described.

International patent application WO 99/61902 A1 discloses a method and a system for identifying analytes and to distinguish them from other analytes. Analytes mean here carried odors, especially in vapor or liquids. In certain cases, a statistical metric is used. A variety of sensors is exposed to different odors and generate according to electrical responses, which are represented as a vector in a d-dimensional space. A statistical metric is optimized in a central computer with respect to selectivity between first and second odor as well as the smallest possible number of detectors. This is implemented mathematically by determining the project axis on a low-dimensional subspace as possible of the d-dimensional space, which has by an optimal separation of records of two different odors. Described sensor types include, inter alia, acoustic, chemical and micro-opto-electro-mechanical devices. The response of all sensors in combination creates a "fingerprint" that can be used to identify the analytes. The examination methods are based on chemical properties, however, not physical, in particular rheological properties. Although, the reduction of the set of sensors serves to achieve faster and more efficient measurements, but no integration into a production process or real time production support is disclosed. The "fingerprint" is also not used in tamper-proof markings of a substance. The signature of a substance is also not process- or machine-correlated.

The U.S. Pat. No. 5,074,158 discloses an apparatus for continuous examination of a powder which is passed through a tube of a production plant. The test result is obtained by optical detection, displayed as an image on a monitor and analyzed by an image analyzer. An identification of the powder is not provided. Furthermore, the measured data sets are not associated or evaluated by computerized algorithms.

SUMMARY OF THE INVENTION

According to aspects illustrated herein, there is provided a system for identifying or distinguishing materials, including at least one local unit, with each local unit having at least one measuring device for detecting at least one respective actual signature for the materials, at least one local computer communicatively coupled to the at least one measuring device, a local database of the local computer for storing and/or processing of the actual signature, at least one center with a server and a central database for storage and/or processing of the actual signatures of the local unit, and, a network, which communicatively connects the local computers of the local unit via the server to the center.

According to aspects illustrated herein, there is provided a method for identifying or discriminating unidentified materials with a system having the steps of acquiring an actual signature among a first quantity k of different measured values of a first unidentified material by at least one user of a local unit of the system, transmitting a request from the at least one user to an operator of a center of the system, wherein with the request is the actual signature, storing the actual signature in non-volatile memory on a server of the center, creating a derived target signature by applying each of a plurality of correlations to the actual signature for at least one target material, wherein the plurality of correlations relate to an extended signature of the target material and wherein the extended signature consists of a second quantity n different measured values and the second quantity n is greater than or equal to the first quantity k, calculating a deviation of each of the derived actual signatures for the material based on the respective extended signature of the at least one target material, and, reporting to the requesting user, for which target materials the respective deviation of a material, based on a target material, is less than one for the target material defined tolerance.

According to aspects illustrated herein, there is provided a method for identifying or discriminating of materials, having the steps of selecting I measurement methods from different measurement methods, wherein the number I is less or equal to m, measuring an actual signature of the material by means of a measuring device for executing the I different measurement methods, generating a derived actual signature per measured actual signature of the material by applying per target material at least one associated correlation of at least one target material, determining a deviation per derived actual signatures of the material of the respective derived target signature of the at least one target material, comparing each deviation with a tolerance specified for the respective target material, and outputting, for which target materials the respective deviation between the target material and material is less than the tolerance of the respective target material.

An object of the invention is to provide a system with several measuring devices for systematic, fast, cost effective, reliable and selective identification and discrimination of various heterogeneous materials, which enhances the selectivity of the individual measurement devices while reducing their measurement effort.

This object is achieved by a system for identifying or distinguishing of materials comprising: at least one local unit, wherein each local unit comprises at least one measuring device for detecting at least one respective actual signature for materials; at least one local computer communicatively coupled to the at least one measuring device; a local data base of the local computer for storing and/or processing of the actual signature; at least one center with a server and a central database for storage and/or processing of the actual signatures of the local unit; and a network, which communicatively connects the local computers of the local unit via the server to the center.

It is another object of the invention to provide a fast, cost effective, reliable method for operating a system for the identification and discrimination of various heterogeneous materials which increases the selectivity and simultaneously reduces measurement effort.

This object is achieved by a method, for identifying or discriminating materials with a system comprising the steps of: acquiring an actual signature among k different measured values of a to be determined material by at least one user of a local unit of the system; requesting of the at least one user to an operator of a center of the system, wherein with the request, the actual signature is transmitted; non-volatile storing the actual signature, provided by the at least one user, on a server of the center; creating a derived target signature by applying each of correlation to an actual signature for at least one target material, wherein the correlation relates to an extended signature of a target material and wherein the extended signature consists of n different measured values and the number n is greater than or equal to the number k; calculating a deviation of each of the derived actual signatures for the material based on the respective extended signature of the at least one target material; and reporting to the requesting user, for which target materials the respective deviation of a material, based on a target material, is less than one for the target material defined tolerance.

A further object to provide a standardized, fast, inexpensive and reliable analysis method that increases in the identification or discrimination of various heterogeneous materials, like powders, which selectivity and simultaneously reduces measurement effort.

This object is achieved by an analysis method for identifying or discriminating of materials, comprising the steps of: selecting I measurement methods from different measurement methods, wherein the number I is less or equal to m; measuring an actual signature of the material by means of a measuring device for executing the I different measurement methods; generating a derived actual signature per measured actual signature of the material by applying per target material at least one associated correlation of at least one target material; determining a deviation per derived actual signatures of the material of the respective derived target signature of the at least one target material; comparing each deviation with a tolerance specified for the respective target material; and outputting, for which target materials the respective deviation between the target material and material is less than the tolerance of the respective target material.

Yet another object of the invention to provide an inexpensive, reliable, flexible, configurable and standardized measurement device, which is suitable for selective identification or discrimination of heterogeneous materials, like powders, to determine reproducible measurement values and with the least possible measurement.

This object is achieved by a measuring device for detection of material properties of materials, the measuring device comprises: at least one test specimen, each for receiving a sample of the material; a plurality of measuring units associated with the test specimen for carrying out I different measuring methods with the sample for detecting an actual signature of the material of at least I time-dependent measurement values, wherein the measuring devices comprise at least: a plunger and a pressure gauge for detecting the applied pressure by the plunger onto the sample; a distance meter for detecting a distance covered by the plunger; an electrical measuring instrument for detecting an electric resistance of the sample; and data acquisition device is electrically connected to the measuring devices for the synchronized detection of the k time-dependent measurement values of the actual signature.

The invention relates to a system for identification or discrimination of materials. The system encompasses of at least at least one local unit and at least a control center. Each local unit includes at least one measuring device for detecting at least one respective actual signature for materials to be determined and at least one of the at least one measuring device is communicatively connected to the local computer with a local database for storing and/or processing the actual signature. The at least one center includes a server with a central database for storing and/or processing of the actual signatures of the local unit. The system further includes a network that communicatively connects the local computer of the local unit via the server to the center.

According to the invention the processing of the actual signatures is preferably carried out according to a method or analysis method described below. In particular, the measuring devices of the local units of the system may include for this purpose a respective selection of u measuring devices for the execution of I different measurement methods for detecting an actual signature of k time-dependent measured values of at least one sample of a material. The selection is made from v measuring devices for executing m different measuring methods for determining a respective extended signature of n measured values for at least one target material. The numbers u, l and k are less than or equal to v, m and n, respectively. A data acquisition device is electrically connected with the u measuring devices for a synchronized detection of the k time-dependent measurement values of the actual signature and the respective local computer.

The system may include altogether of all measuring equipment to perform all m different measuring methods for determining a respective extended signature of n measured values for at least one target material. Consequently, the extended signatures may be collected by the system and stored non-volatile in the central database. For this purpose it is not necessary that all the local facilities have all the measuring equipment. The center can include at least one other measuring device with all measuring devices or only a selection thereof.

The invention further relates to a method for operating a system for identifying or distinguishing materials. The method has various steps.

Firstly, the acquiring of an actual signature of k different measured values of a material to be determined by at least one user of a local installation of the system. The next step is that the at least one user requests at an operator of a center for the system, that the actual signature is transmitted upon the request. A non-volatile storage is provided on a server of the center for storing the actual signatures transmitted by the at least one user. Creating a derived target signature is carried out by applying an actual signature for at least one target material per a correlation. The correlation is based on an extended signature of a target material. The extended signature consists of n different measured values. The number n is greater than or equal to the number k. This is followed by calculating the derived actual signature for the material according to a deviation based on the respective extended signature of the at least one target material. It is reported via return to the requesting user for which target materials the respective deviation of a material of a target material is less than a specified tolerance for the target material.

These actual signatures can be linked by at least one user and/or by the operator with metadata relating to the requesting user and/or the operator. For example, the operator or the user can verify with each other, in terms of a "peer review" that the measurement data of an actual signature and the result is linked as metadata with the actual signature. Further metadata include: an operating time at which the actual signature and their measured values were collected; a measurement time for each of the u measuring devices of the actual measurement; a user ID of the user executing the measurement; a place where the measurement is carried out; an identification of the material (for example, the supposed material composition to be determined); an identification of a sample or batch of material; a weight of a sample to be measured of the material; an identification per each measuring device, and/or remarks of a user with regard to measurement conditions (ambient temperature, humidity, time and events during the storage of the material) or the measurement objectives and specifications for application by the requesting user. Another metadata may relate to a classification of the requesting user with regard to the trustworthiness of a data source. The metadata may in particular include a test report. This test report includes at least the respective deviation and/or a certificate of quality of the material, the certificate donor and/or the measured actual signatures. The requesting user can report back to the operator, whether the identification or discrimination of the material is correct according to his knowledge and opinion. The feedback is preferably in the form of electronic metadata.

The response of the operator to the requesting user can also be customized to their needs. For each user, and for at least one target material, the operator can optimize the associated correlation and the corresponding derived target signature for a combination of optimization criteria with associated weighting. Preferably, this optimization is done with an algorithm that runs on the server in the center of the system. The weights are modified, for example, based on metadata.

The more often the inventive method is carried out, and the more users participate, the more the central or local databases expanded trained and/or personalized. The operator and/or a user can with the use of the metadata and/or the already measured actual signatures extend those actual signatures in order to be detected by additional methods of measurement readings. This requires a new optimization of the derived target signatures and the correlations for at least one target material. Alternatively, a previously not listed material on the local or the central databases can be listed as a new target material.

The inventive analysis method is used for identifying or discriminating in particular heterogeneous materials. For example, it can be used in a system for identifying or discriminating of heterogeneous materials or a system for processing a product. The system for processing the product is, for example, a plasma coating system which applies a coating onto a material surface, wherein a powder is introduced into a plasma stream. For example it can be used for quality control or material control. According to the analysis method, firstly m different measuring methods are applied on one or more target materials. A target material is characterized in that it is suitable for product processing. Each of the m measurement methods records at least one measurement value. According to the invention, all measurement values taken for a target material, are aggregated in a data vector with at least n=m measurement values. The dimension of the associated vector space corresponds to the number n of measurement values. This dimension is strongly correlated positively with the selectivity of the measurement method. Thus, small changes can be reliably detected in a material. From each of these data vectors an extended signature ("fingerprint") is created. The m measurement methods are selected such that the extended signature is characteristic for the target material, so that it is clearly determined or over-determined in the mathematical sense. In a further step a database is created from the target signatures of all target materials.

In a subsequent optimization step, a selection of l measurement methods is made for each target material from the m measurement methods, where the number is smaller than or is equal to the number m. Accordingly, this selection of l measurement methods generate target signatures. The target signatures, listed as data vectors, have a lower or at maximum same dimension as those extended target signatures generated by the full set of m measurement methods extended target signatures. These target signatures are either measured again or obtained by omitting those n-k values, which have not been captured by l measurement methods. For each pair of extended target signature and target signature a correlation is determined as well. By using this correlation to the signature a derived target signature is generated. The selection of l measurement methods and the associated correlation are iteratively optimized. For example, the number or the total effort in measurement of the measurement methods is minimized. According to the invention, the applying of the selection of the l measurement methods is at least ten times faster than applying the m measurement methods.

In the next step, a target database is created. In it are stored for each target material a set of derived target signatures, selections of measured values and the required methods of measurement and/or correlations for their collection.

In a further step, at least an undefined material is checked with respect to its suitability for processing in an apparatus for product processing. For it, an actual signature is measured in each case. Then, a derived actual signature is generated by applying the respective correlation to the actual signature of each relevant target material. Then the deviation is determined of the derived actual signatures of each material from the derived target signature of the at least one target material. Ultimately, the deviation is compared with a tolerance which is specified for the device for processing the product, the target material and/or the product to be produced. The deviations are preferably determined from the vector norm of the difference between the derived target signature of a target material and the derived actual signature of a material.

If the deviation of a material smaller than the tolerance, the material is processed in a final step in the apparatus for processing product, released for processing or logs the processing of a shared material.

The material properties and material values to be tested include, in particular, the composition of the material or its surface, the rheological properties, the electromagnetic properties, mechanical properties, optical properties, the bulk density, the granularity of the material, the size distribution of the particles of the material, the geometric properties of the particles, the magnetic susceptibility, the high-frequency properties, the electrical conductivity, the sublimation or melting temperature, the weight and/or specific gravity of the material, or the complex impedance subjected with alternating current. Furthermore, several measurement values are recorded in causal dependence on each other, for example the on the material applied compression force as a function of the compression path. Few characteristic derived measurement values or parameters can be determined from the chronological sequence of such dependencies.

The combined measurement methods according to the invention include, in particular chemical measurement methods; rheological measurement methods; optical measurement methods; high-resolution color photography; thermodynamic measurements; X-ray diffraction studies, determination of the magnetic material properties; detection geometric distribution functions and data analysis methods for extracting derived measurement values and parameters, respectively. A given measurement method can be performed by various successive calibrated measuring devices. A combination of several measurement methods is far superior to single measurement methods especially in heterogeneous mixtures of materials with respect to the separation efficiency.

The optimization of a set of derived target signatures, selections and/or correlations for each target material can be performed in particular by means of a computerized algorithm. The algorithm can be, for example, an artificial neural network (ANN), a genetic algorithm, a principal component analysis, a Monte Carlo algorithm, a simulated annealing algorithm, a Fuzzy Logic algorithm or a K-nearest neighbor algorithm.

The optimization can be carried out according to the invention for a combination of optimization criteria. The optimization criteria may also be provided according to their relevance to the processing of material in a device for processing product with associated weights.

The optimization criteria may include: a sufficiently small first deviation for processing in the apparatus for product processing between the signature and the signature derived for a particular target material; the relevance of the properties of a target material for processing in the apparatus for product processing; the relevance of the collected measurement values by the measuring methods for the processing in the apparatus for product processing; the measurement time of each of the/measurement methods and their cumulative measurement time, taking into account that some measurement methods can be executed in parallel; the costs of measurement of the/measurement methods and associated with a measurement method the equipment expenditure; the integration of the measurement methods in the process of product processing; the specifications of the processed product; the environmental influences on the device for product processing; the statistical plausibility of measurement values to avoid "outliers". A measurement value can be, according to the invention, a single measurement or a statistically meaningful data ensemble of repeated measurements.

It is usually too burdensome to constantly or randomly carry out several complex methods for quality assurance in a parallel running production process.

With the combination of measurement methods that are inexpensive and fast and are performed continuously on the running process or by sampling at high frequency, using methods which are laborious, time consuming and expensive and, for each material composition performed rarely or once, a material characterization is given with high selectivity.

According to the example of a simulated annealing algorithm, the optimizing can be done according to several optimization criteria and a total energy function is determined. Each optimization criterion provides an energy contribution. Depending on the relevance of the optimization criterion the energy contribution is weighted. For example, the melting point of the material may be irrelevant for a production process. His energy contribution is weighted accordingly very low or with a factor of zero. If the measurement time or cost of a particular measuring method are process-critical, the corresponding energy contribution is weighted correspondingly high. The total energy function can be applied to the optimization criteria as variable, like a high-dimensional energy landscape. In this landscape, the algorithm determines a local minimum corresponding to an optimized set of parameters. The optimization is done via an iteration of random steps. With rising energy difference between the source and target parameter set of the random step, the target parameter set is assumed to be less likely. Consequently, not necessarily the globally best parameter set, but only one for the production process sufficiently suitable parameter set is determined. If many material properties are little or not relevant to the process, a wide class of suitable process materials is defined with respect to the optimization underlying target material. If, however, all material properties are high weighting, all measurement methods are selected (l=m), so that the selectivity of the material identification and discrimination increases at the expense of measurement time or measurement costs.

In one embodiment of the invention, a selected subset of reference data sets is stored in a database. The database contains reference data sets, each consisting of: choosing the measurement methods, the target signature, the correlation and/or the derived target signature of at least one target material. Similarly, audit records can be recorded in the database during the processing of a material, which are signatures, derived actual signature and/or the deviations.

In a further inventive embodiment, the audit records in the database will be transmitted automatically via a digital network to a further external database. This external database, for example, is in the territory of the production supervisors or the manufacturer of the device for product processing. For protection against manipulation, the audit records can be transmitted in encrypted form. The location of the external database can locally be anywhere and be connected, for example via radio communication or the internet with the device for product processing.

In addition, the audit records can be used on the database as a control parameter for a control circuit in the processing in an apparatus for product processing.

Furthermore, on an external storage medium (the system independently) selected target data sets and/or audit records can be stored. This external storage medium is connected to a bundle, a packaging and/or a batch of a target material or a material. The data can be read by appropriate means. A target data to the external storage medium indicates, for example, with which target material and its associated set record a material is to be matched. A set of test results on the external storage medium, for example, functions as a "fingerprint" for a material.

The external storage medium may be a Radio-Frequency Identification (RFID) chip on which the data records are stored in the form of RFID tags. Additionally or alternatively, the external storage medium also can be a label on which the data set are saved in alphanumeric and/or in barcode form.

In a particular embodiment, the selection of the/measurement methods is optimized that the fitness of one or more materials for processing in the apparatus for product processing can be checked during the ongoing production process. Ideal would be a continuous check, wherein the check, considering the typical processing times, takes place in short intervals or in real-time. To speed up the entire measurement process different measurement methods can examine different samples of a material in parallel.

According to the invention, the applying of the selection of the k measurement methods is at least ten times faster than applying the m measurement methods.

Furthermore, a data processing device can read the test database and make sure that the measured values contained in the test database are not collected redundantly. A redundant collection can occur, in case measured value of a material is to be measured in comparison with several target materials. If a measured value is already in the test database, the data processing means activates a reduced set of controls u measuring devices for performing the selection of the measuring methods on a material such that the measurement value is not collected again.

The invention further comprises a system for product processing. It includes an apparatus for processing product for processing at least one indefinite, heterogeneous material. The system is further characterized by a set of u measuring devices, wherein each determines an actual signature for the at least one material. It also includes a data processing means that is communicatively coupled to the set of u measuring devices. The data processing means is adapted to perform the following operations: storing each of a derived target signature and one a correlation for at least one target material which is suitable for processing the product; the application of the correlation for each target material onto the actual signature of each material to calculate a respective derived signature; and storing a log of audit data sets. The audit data sets comprise at least the difference between the derived target signatures and the respective derived actual signature. Additionally or alternatively, the system may also have a control unit which is communicatively connected to the data processing means. The control unit may generate control signals from the audit records and transmits it to the device for product processing.

In addition to the described system external system 91 can be provided. The external system has a set of v measuring devices, wherein each generates a characteristic signature of the at least one target material. The number v is here greater than or equal to the number u. In addition, external system 91 includes computer 71 with which by means of an algorithm the target data sets are generated from the signatures. The target data sets are in turn composed of derived actual signatures, a correlation with an actual signature and/or the actual signature itself. Furthermore, external system 91 includes storage medium 72 for storing the target data sets and data connection 73 for transmitting selected target data sets to the data processing or the first storage medium. The external system is designed to be operable time and place independent of the system for processing material.

In an example embodiment, the data processing means comprises an external storage medium. On the external storage medium, selected target data sets for at least one target material and the log of audit records of selected materials are stored. Further, the data processing system comprises a data processing means to apply a correlation of a reference material onto an actual signature of a given material.

The external storage medium may be readably connected to a bundle, a packaging and/or a batch of a target material or a material. It can thus contain information on how a given material has to be checked. Furthermore, a test result can also be saved on the external storage medium as a "fingerprint".

In particular, the external storage medium is configured as a readable and/or writable Radio-Frequency Identification (RFID) chip. In this case, the data processing system comprises a unit with a suitable frequency-tunable antenna for reading and editing and writing data on the RFID chip.

For the purpose of the tamper resistant remote monitoring of the production, the audit records are transmitted in addition via a remote data connection to another external storage device. In particular the data can be sent in encrypted form. As a remote data link any radio standards (e.g. SMS) or the Internet can be used.

The invention is particularly suitable for coating processes of substrates. Particularly suitable materials for coating are for example powdered alloys, powders, powder mixtures, granules, pastes, solutions, suspensions or dispersions, or a mixture thereof.

In an example embodiment, a supply unit is provided to supply at least one material to the apparatus for product processing. First, the result of the comparison between the deviation and the tolerance specified for the apparatus for product processing and the target material is communicated to the control unit. The supply unit is communicatively connected with the control unit. In dependency from this result the control unit controls the flow of material through the supply unit.

Also, the invention relates to a measuring device for the detection of material properties of materials which is used in particular in the local units and the center of the above-described system for identifying or distinguishing of materials and for carrying out the method according to the invention. The measuring device comprises at least one test specimen, each for receiving a sample of material. Several measuring units are assigned to the test specimens. The measuring devices are used to execute l different measurement methods on the sample in order to detect an actual signature of the material from at least/time-dependent measurement values. The measuring units comprise at least: a plunger and a pressure gauge for detecting the applied pressure P acting by the plunger on the sample; a distance meter for detecting a distance traveled by the plunger; and an electrical measuring instrument for detecting an electrical resistance R of the sample. Further, the measuring device comprises a data acquisition device which is electrically connected to the measuring unit for synchronized acquisition of the k time-dependent measurement values of the actual signature.

In particular, all measurements are referenced to a common spatial axis. For this purpose, the measuring units for example are designed and arranged such, that the pressure P, impinged by the plunger on the sample, the traveled distance by the plunger and detected by the distance meter and the electric resistance R determined by the electrical measuring instrument along an axis, are registered.

Data acquisition device can include a standardized data interface, such as an USB port, for transmitting the actual signature to a data processing device.

In addition, the set of u measuring units of the measuring device can also be an optical measuring instrument for optically detecting a surface of the sample, an active or passive acoustic measuring instrument for measuring the acoustic residual spectrum and resonances of the sample respectively, a thermometer for detecting a sample temperature or an ambient temperature, a scale 416 for detecting a weight of the sample; and/or a hygrometer for detecting a humidity in the measuring device.

The data acquisition device is communicatively connected with a local computer. The local computer can record, analyze and store the measurement values, which that have been recorded with the u measuring units. For example, the local computer can fit a measurement diagram of the pressure as a function of the distance with a sigmoid function and extract the fit parameters. These fit parameters can be included into the determined actual signatures instead of direct measurement values. Furthermore, the local computer can serve to detect related metadata of a user of the measurement unit.

The analysis method and system according to the invention can be used for examining identifying or discriminating of powdery alloys, powders, powder mixtures, granules, pastes, solutions, suspensions, dispersions, or a mixture thereof. They can also be applied to several different materials in order to produce material mixtures, alloys or composite materials in a logged and monitored manner through the process of material processing.

By way of example, an embodiment of the invention is explained with the example of the choice l=3 from m=5 measurement methods.

A sequence of five different measuring methods is applied to a powder. The correlation between the results of the measurement methods is not empirically or not known exactly.

The first measuring method is an optical characterization. The powder is applied evenly on a transparent plate and an optical image is captured with a flatbed scanner. The flatbed scanner can be calibrated with a synchronously recorded color normal. From this image, characteristic data such as the average color values (RGB, etc.), and derived parameters that describe the spatial distribution of these color values are obtained. Similarly, the optical characterization can be carried out with a suitable test specimen, which has, for this purpose, a transparent window and an associated camera records the color values.

The second method is a mechanical characterization. A sample of the powder is uniaxial compression loaded in the test specimen and the curve of press capacity and press stroke are recorded. Such a curve typically has a sigmoid course and can be described by a few parameters.

The third method is an electrical characterization. In parallel with the application of the second method, the dependence of the electrical conductivity of the powder can be recorded in dependence on the press capacity. This curve has also a characteristic sigmoid course and can be described by a few parameters.

The fourth method is a geometric characterization. With a statistic microscopic analysis method, the particle size distribution is recorded. With irregularly shaped particles, it is advisable, for the sake of simplicity, to state an equivalent diameter to characterize the size. In case the shape of the particle has also to be taken into account a shape factor can be defined as the ratio of the two equivalent diameters, such as volume equivalent and surface equivalent ball diameter. The geometric data are well described by, for example, a medium shape factor and the distribution parameters $D10$, $D50$ and $D90$.

The fifth method provides information about the chemical composition of the material in volume. By a chemical analysis, for example, the elemental composition of the material being tested.

The first, second and third method are quick and simple to perform. In contrast, the fourth and fifth method requires considerable preparative and instrumental effort. A powder, for example, is definitely described by a signature, which is generated with these five methods, as feature vector in a 50-dimensional measurement space. The subspace from the measured values of the first to third methods has, however, in this example, only 14 dimensions.

Although the measurement methods are different, their results are correlated in a complex, unknown, empirically quite difficult to grasp manner. For example, the color of a metallic powder, which is measured with the first method, depends on, the oxide content and the oxidation of the surface of the powder particles respectively, which is determined with the fifth method. Analogously, the oxide content has an influence on the electrical properties, which are measured by means of the third method.

Because of these "hidden", complex cross-dependencies, it is possible to supplement an incompletely measured feature vector. Algorithms such as "artificial neural networks (ANN)" are particularly well suited for the complement of the property space. For this the full set of methods is applied to a material several times and there from the statistically reliable complete feature vector is derived. The neural network is then trained so that even with input of an incomplete feature vector a complete feature vector is reconstructed as an output. In practice, it is advantageous to use the fast and simple measuring methods for the recovery of the incomplete feature vector.

For quality assurance, it is possible to set a derived target signature and an appropriate metric for a maximum tolerance of the measured derived actual signature, which is acceptable for a given production process. Depending on the choice of tolerance as well as a suitable choice of measurement methods and the optimization of the coefficients, the algorithm yields, based on an incomplete set of measurement data, actual signatures, a reconstructed feature vector, the derived actual signature, which differs from the target signature of a target material with sufficient selectivity.

In addition to quality assurance, the method can also be used to determine a "fingerprint" for a material. This "fingerprint" can be stored on the material container in alphanumeric form, or as an RFID tag and serve to ensure the originality of the material. The originality test can be already with the reduced set of measurement methods, like the first to third measurement method, and thus be made quickly and easily.

In particular, for example powder materials, can be classified tamper-proof. The classification can be hold in a unique numeric value. This value can, for example, be hold via barcode or RFID tag or even noted alphanumerically on the material bundle to ensure batch quality or to prevent deliberately use of inferior materials from unreliable sources. If the full feature vector is stored as a "fingerprint" on the material bundle, the algorithm can be formulated in very general terms and is very fast convergent even in very diverse discriminatory materials.

These and other objects, advantages and features of the present invention will be better appreciated by those having ordinary skill in the art in view of the following detailed description of the invention in view of the drawings.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION OF THE INVENTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspect. The present invention is intended to include various modifications and equivalent arrangements within the spirit and scope of the appended claims.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
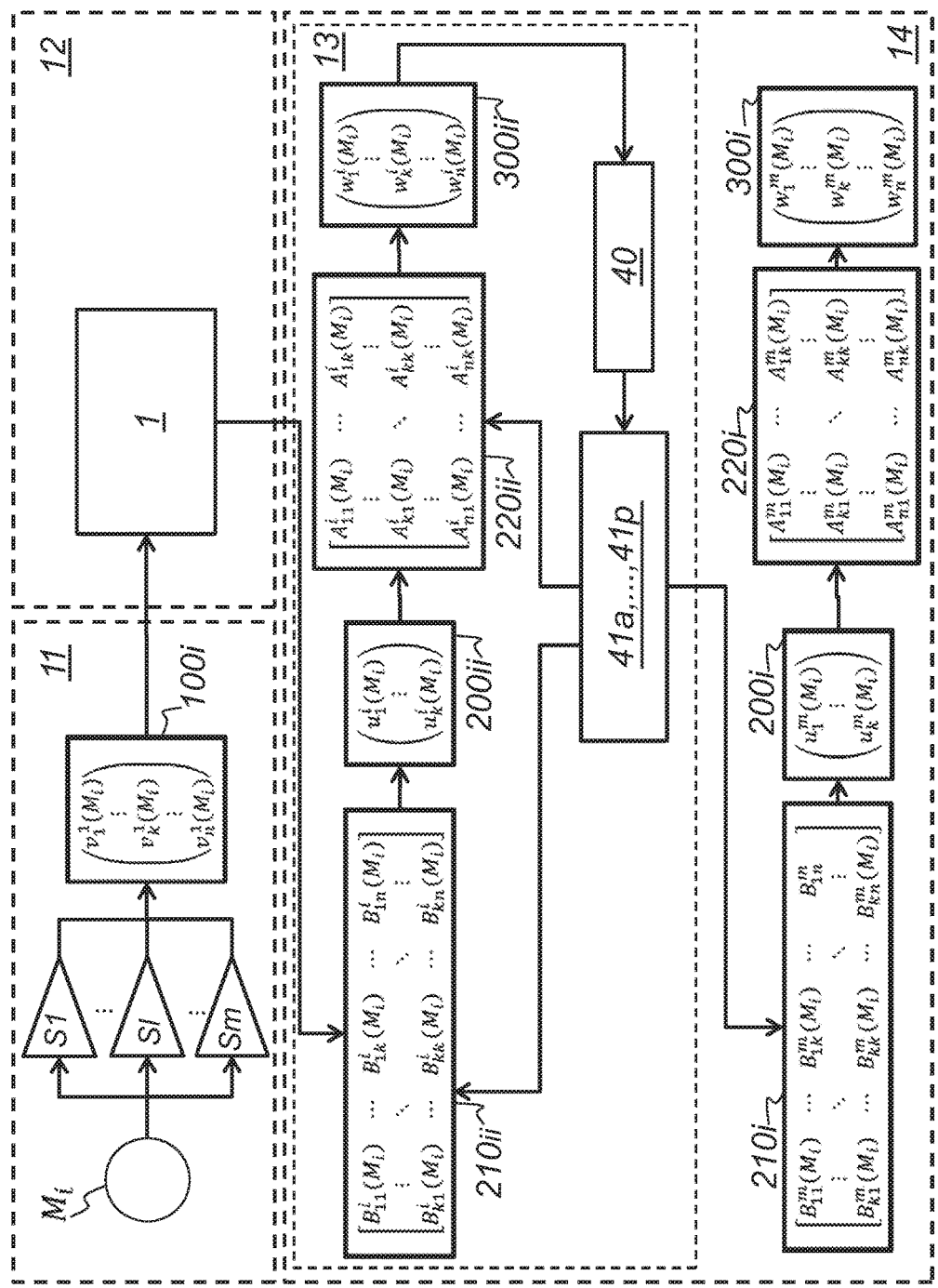
FIG. 1 is a schematic representation of the optimization method according to the invention.

FIG. 1 shows an embodiment of the inventive optimization method in a schematic representation. In step 11, one or more target materials $M_i$ are selected and measured with a set of m different measurement methods S1, . . . , Sm. Each measurement method S1, . . . , Sm appoints one or several different measurement values. Each measured value can be determined several times and combined statistically to a safe reading. For data analysis, the measured values are combined to form a feature vector. The m measurement methods S1, . . . , Sm are chosen such that the feature vector of target material $M_i$ represents a unique, characteristic extended signature 100i.

In step 12, database 1 is created from extended signature 100i for each target material $M_i$.

In step 13, a random or empirical based start selection of I of the m measurement methods S1, . . . , Sm is made, wherein I is less than or equal to m. This is iteratively optimized. In i-th optimization iteration 13, i-th selection 210ii of measurement methods is initially specified, preferably in matrix notation. Applying selection (matrix) 210ii to extended signature 100i generates i-th target signature 200ii for target material $M_1$, with lower or equal dimension. Then, an algorithm generates i-th correlation 220ii, their application to the signature generates i-th signature 300ii derived from the same dimensionality as extended signature 100i. By combination 40 (see FIG. 2) of optimization criteria 41a, . . . , 41p, optimization method 50, like that of an ANN algorithm, optimizes iteratively i-th selection 210ii and correlation 220ii until the global or a local optimum is determined. Optimization 14, for example, can be terminated by reaching a specified convergence criterion or after a fixed number m of optimization iterations 13. An optimum has selection 210i of I measurement methods S1, . . . , Sl, target signature 200i, correlation 220i and derived target signature 300i for a respective target material $M_i$. This selection 210i can be any combination of the m measurement methods S1, . . . , Sm. Similarly, the number I of selected measurement methods S1, . . . , Sl can be different at start selection and optimized selection 210i. In an embodiment, weights and cross connections are not included in selection 210i. These can equally be considered in correlation 220i. This means, that selection 210i may be represented as a diagonal matrix with diagonal elements of 1 or 0. In this case, selection 210i indicates directly and without computing time on which measurement value is to be collected with which measurement method S1, . . . , Sm.

Figure 2:
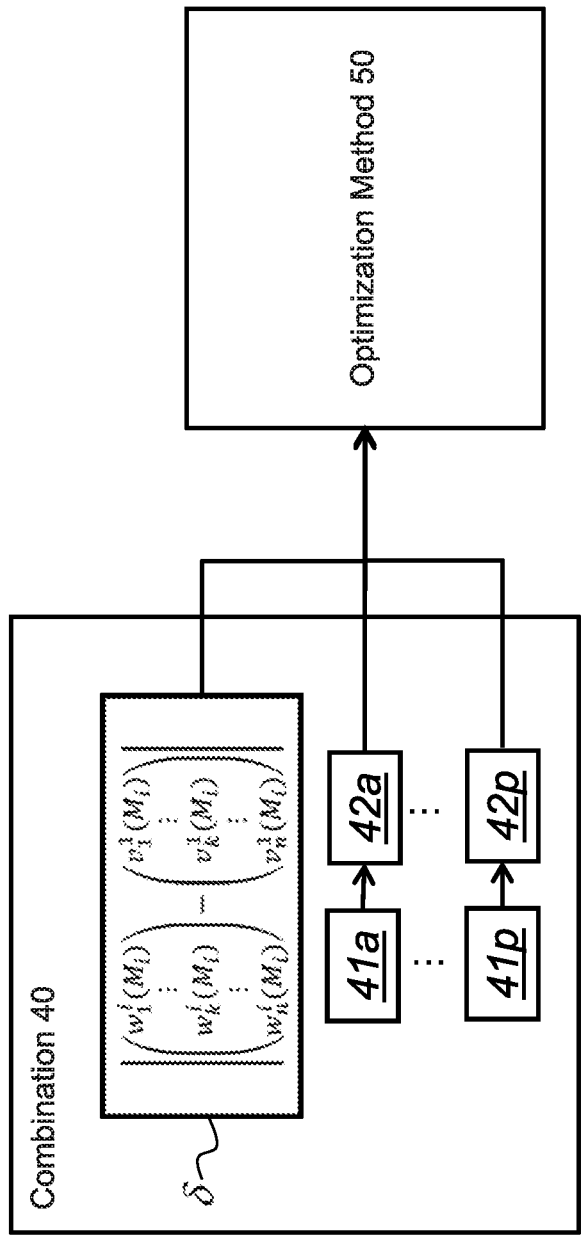
FIG. 2 is a schematic representation of the weighted optimization criteria and the optimization method.

FIG. 2 illustrates combination 40 of optimization criteria 41a, . . . , 41p and how they influence optimization method 50. The selection of optimization criteria 41a, . . . , 41p depends, according to the invention, on a purpose. The purpose may be, for example, to coat a substrate in a plasma-assisted coating system with material $M_j$, which exhibits specific characteristics of target material $M_i$, and the rapid, accurate process-supporting quality control of each coating process. In addition, the optimization criteria are weighted with a respective weighting 42a, . . . , 42p, that optimization step 14 (see FIGS. 1 and 3) is better tuned to the purpose. Accordingly, special process relevant material properties are weighted high (by a factor close to 1) and process not relevant material properties are weighted with a factor close to zero. Furthermore, time-consuming or costly measurement methods S1, . . . , Sm can be weighted less, so it is less likely to be included in optimized selection 210i. In particular, the optimization refers to the minimization of distance δ from extended signature 100i to derived target signature 300i of target material $M_i$. Distance δ indicates the tuning error with which one can reconstruct extended signature 100i from target signature 200i. The optimization result can thus be a compromise between selectivity, measurement cost or measurement speed.

Figure 3:
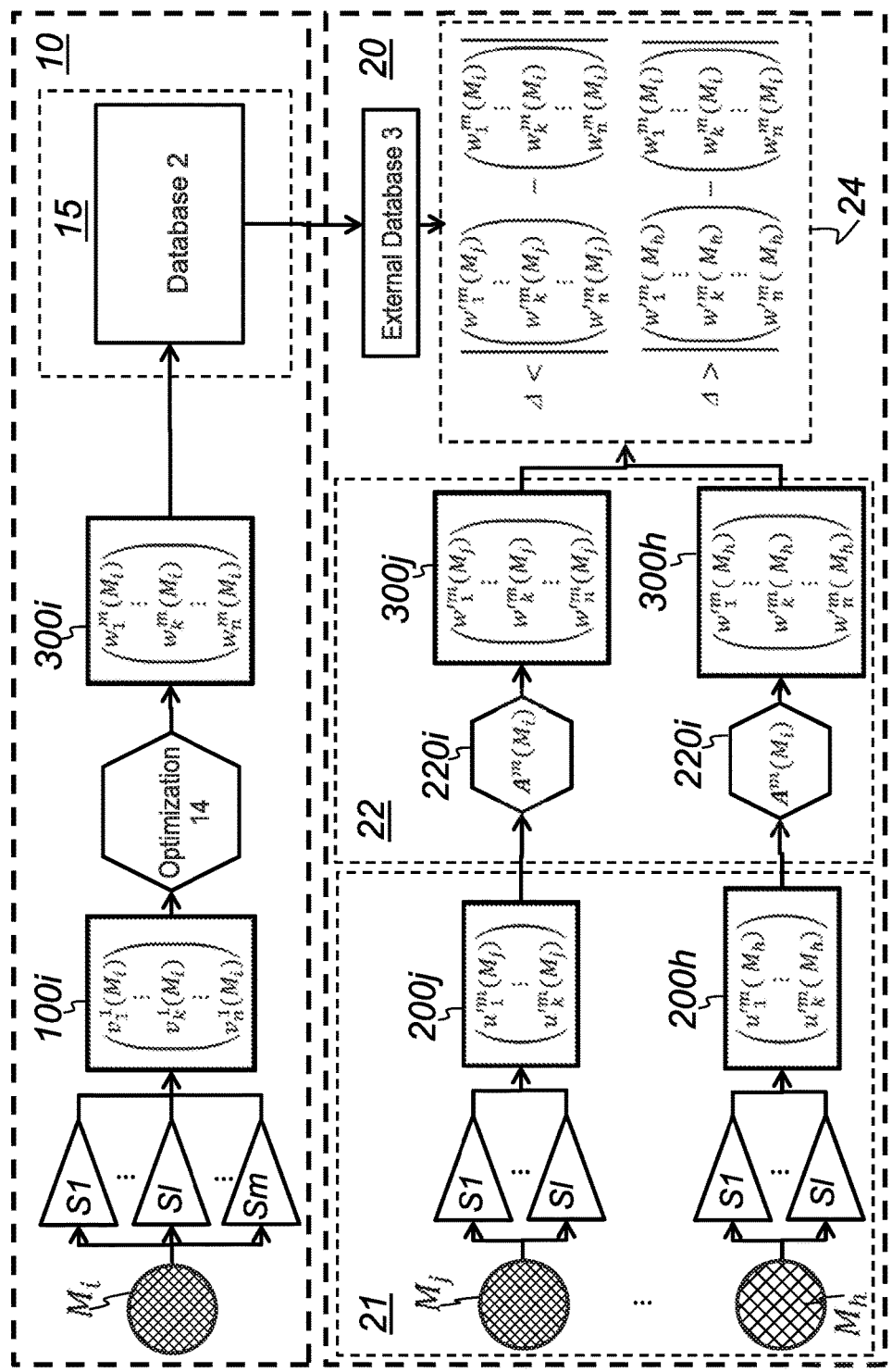
FIG. 3 is a schematic representation of the analysis steps according to the invention for identifying or distinguishing of a material from and against target materials, respectively.

FIG. 3 is a schematic representation of the inventive analysis method steps for identifying or distinguishing a material from or against target materials. The "off-line" sequence of steps 10 includes steps 11, 12, 13 and 14, which have already been described with respect to FIG. 1 and FIG. 2. In addition, the optimization results and derived target signatures 300i for each target material $M_i$, are stored in step 15 in a target database and are transmitted to external database 5. Contained thereon is, for example, all information about suitable target materials for processing in a production process. Furthermore, a procedural requirement is included, how material $M_j$ matches against the target materials.

Then, "in-line" step sequence 20 is executed. The term "in-line" designates that step sequence 20, in contrast to the "off-line" step sequence, is provided for the integration into a production line.

A particular advantage of the analytical method and system of the invention is that an automated process control is possible. In first step 21, selection 210i of I measurement methods S1, . . . , Sl is applied to material $M_j$, $M_h$ to be worked on or to be tested for each of the relevant target material $M_i$. Out of it, based on target material $M_i$, an actual signature 200j and 200h are generated, respectively. In the subsequent step 22, correlation 220i is applied to actual signatures 200j and 200h, respectively, to generate derived actual signatures 300j and 300h. Alternatively, optimization step 14 can be performed also at each test step. In the final step 24 identifying and distinguishing of materials $M_j$, $M_h$ of target material $M_i$ and the qualification examination for processing takes place respectively. For this, the vector norm of the difference between the derived target signature 300i with the respective derived actual signature is 300j or 300h preferentially formed. In this case, the derived target signature 300i and/or the correlation 220i are taken from the external database 3. This deviation δij is compared with tolerance Δ. If deviation δij for material $M_j$ is less than tolerance Δ, it is considered that material $M_j$ belongs to a material class defined by target material $M_i$ and suitable for a production process respectively. If deviation δij for material $M_h$ is greater than the tolerance Δ, it is considered that material $M_h$ does not belong to a material class defined by target material $M_i$ and is not suitable for a production process respectively.

Figure 4:
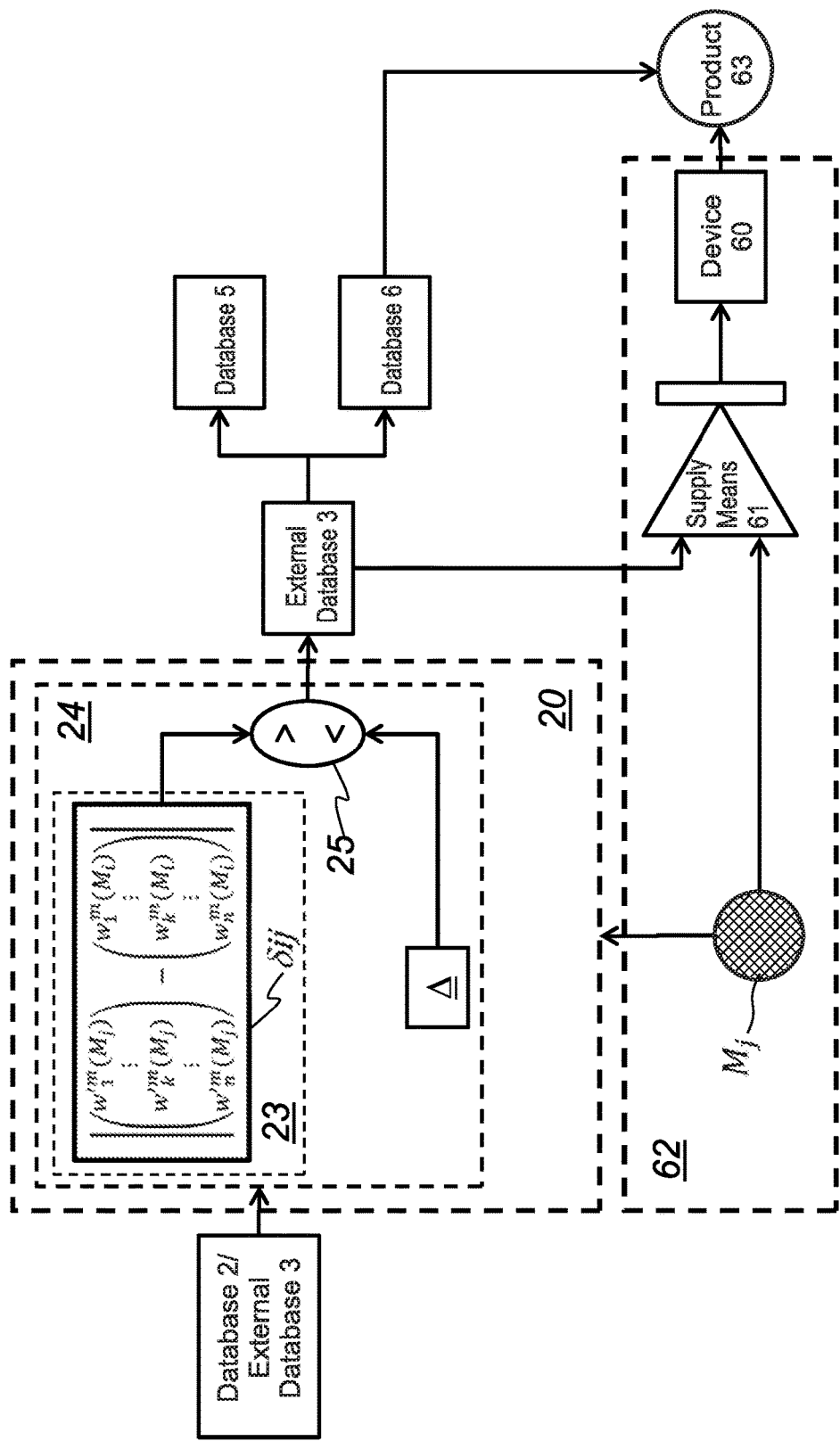
FIG. 4 is a schematic representation of the analysis method of the invention.

FIG. 4 is a schematic overview of the analysis method according to the invention. Target data sets are drawn from the target database 2 or the external database 3 and "in-line" step sequence 20, described in FIG. 3, is performed. Step 24 will be described in more detail here. After comparing 23 of the actual signature 300j and the target signature 300i and norm-building therefrom, it follows the scalar capability 25 with the tolerance Δ. The test result and/or the determined and derived signature 300j and actual signature 200j respectively are documented on the external database 3. These audit records can then be transmitted to another external database 5 or product database 6. Audit records from product database 6, for example, can be stored on a label or an RFID chip in an alphanumeric manner as a barcode or as digital data, which can be readably joined with a product 63, in order to definitely mark and identify the product 63. The further external database 5 is preferably in the domain of the operator or manufacturer of device 60 for product processing. The continuous, preferably encrypted communication of audit records to the other external database 5 provides the opportunity for automated, transparent and tamper-proof quality control. Tolerance Δ can be, depending on the objective of the inventive analysis method, specified or dynamically adjusted. If it is dynamically adjusted by the operator of apparatus 60 for product processing, it is recommended to store their variation in time on external database 3 and to transmit it to the other external database 5 or product database 6.

Parallel processing 62 of material $M_j$ takes place in device 60 for product processing in order to obtain product 63. Supply means 61 can control the supply of the material $M_j$ in response to the audit records in the external database.

Figure 5:
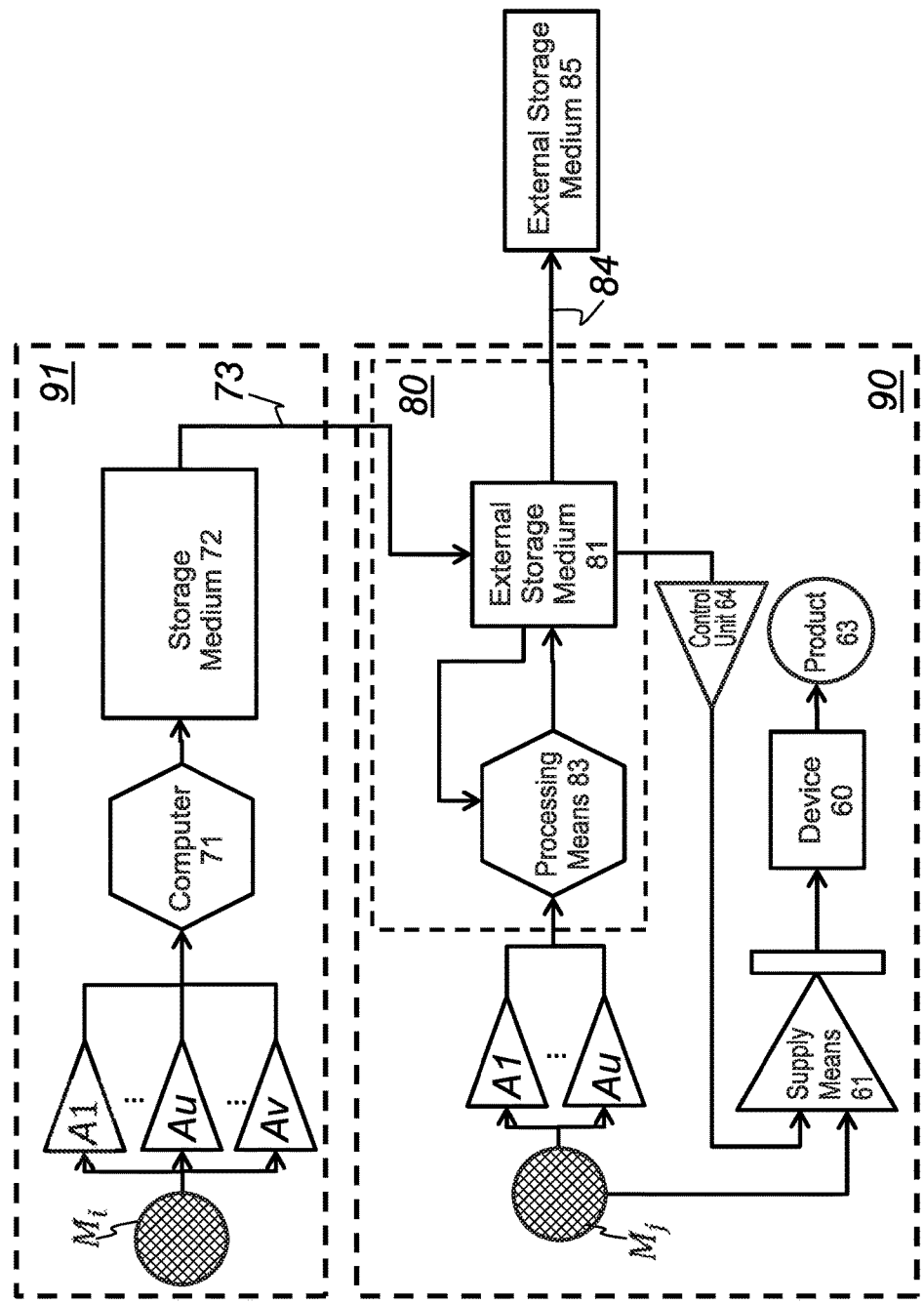
FIG. 5 is a schematic representation of the processing system according to product.

FIG. 5 shows a schematic representation of the inventive system 90 for product processing. For material $M_j$, intended for processing, signature 200j is generated by a set of measuring units A1, . . . , Au. Data processing system 80 reads actual signature 200j of measuring units A1, . . . , Au and target records from external storage medium 81. Furthermore, a data processing device 83 of the data processing system 80 checks the material $M_j$ by performing "in-line" step sequence 20 of FIG. 2. The results are reported as audit records to external database 3 and are transmitted, preferably encrypted, via remote data link 84 to another external storage medium 85. In addition, the audit records are transmitted to control unit 64 which regulates supply means 61 of device 60 for product processing for material $M_j$ in dependency of this audit records. In case the examination results in, for example, material $M_j$ not being suitable for processing 62 in device 60 for product processing, the supply of material $M_j$ is stopped, so that it will not be processed into product 63.

Figure 6:
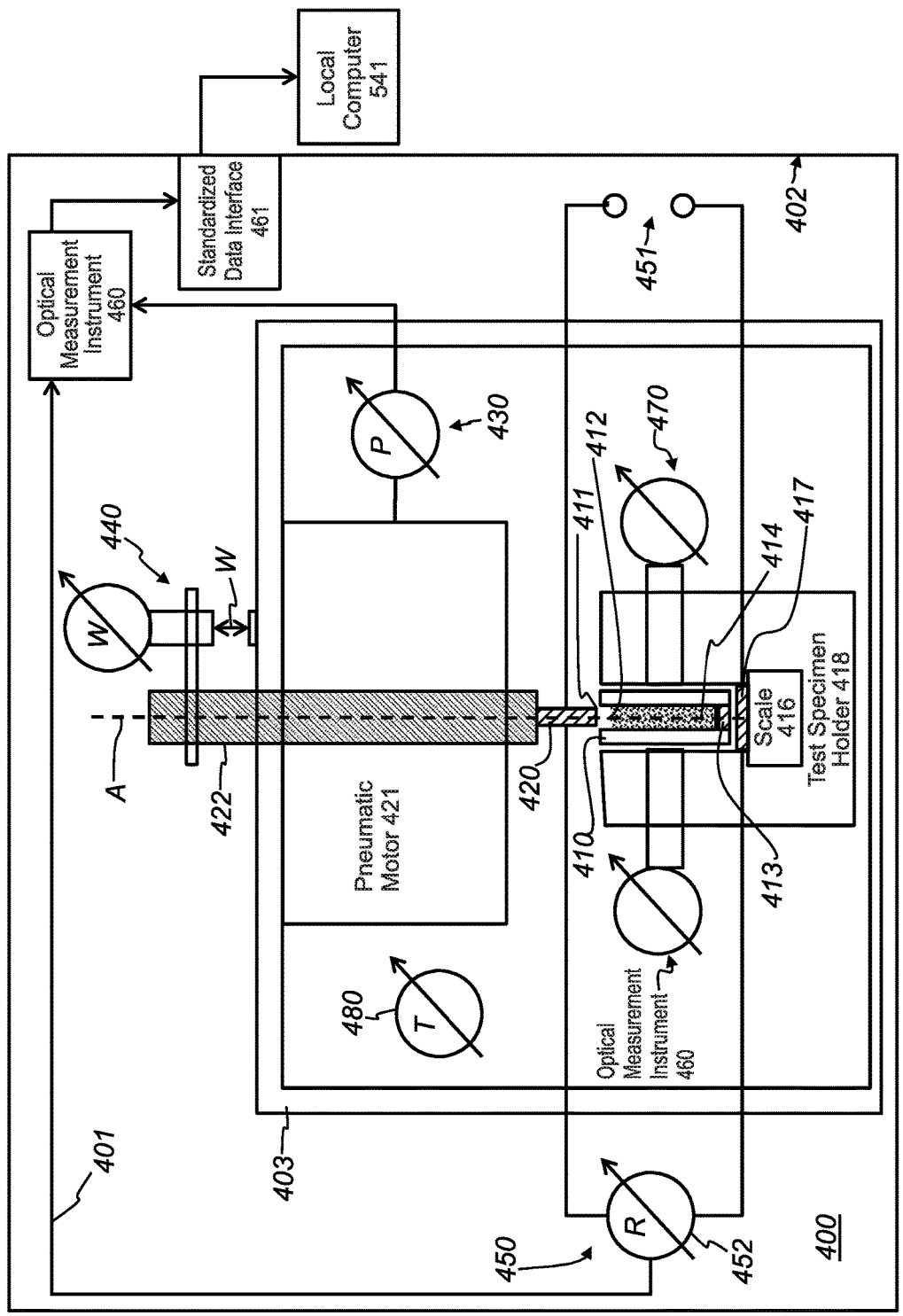
FIG. 6 is a schematic representation of a measuring device according to the invention for determining material properties of materials.

FIG. 6 is a schematic representation of an embodiment of measuring device 400 for the detection of material properties of materials $M_j$. Measuring device 400 may be received in externally accessible housing 402. In particular, measuring device 400 is suitable for compressible materials $M_j$, such as powders or gases, and in particular for electrically conductive powders. However, little compressible fluids can be measured in general. Suspensions of solid particles in liquids can, according to the invention, be dried at least partially under controlled and reproducible conditions, so that they are available in powder form.

Measuring device 400 comprises an electrically insulating test specimen 410 with a lower electrically conductive shutter 413, upper opening 411 and cavity 412 for receiving sample 414 of material $M_j$. Test specimen 410 is preferably of cylindrical form. In order to obtain comparable and reproducible results, the initial conditions are set during the filling of sample 414 in test specimen 410 in a defined manner. For example, sample 414 has a defined weight of powder. The powder can be weighed by means of a balance. Preferably, it is filled by a powder metering apparatus (not shown), which makes not only the weight but also rheological relevant variables such as the compacting of the powder or measurement-related variables such as the shape of surface 415 of the powder or air pockets in specimens 410 controllable. The validity of the measurements increases, for example, if the same or a similar powder metering apparatus charges device 60 for product processing. Test specimen 410 is sitting in test specimen holder 418 during the measurement. Test specimen 410 and test specimen holder 418 can have corresponding positioning elements (not shown) in order to obtain a definite positioning of test specimen 410 in test specimen holder 418.

The measuring device 400 further comprises a plurality of measuring units A1, . . . , Au associated to test specimen 410 for the execution of I different measuring methods S1, . . . , Sl on sample 414 in order to detect actual signature 220j of material $M_j$ of at least I time-dependent measurement values.

One of the measuring units A1, . . . , Au is composed of an electrically conductive plunger 420 and pressure gauge 430 for detecting the pressure P acted upon sample 414 by plunger 420. Plunger 420 is formfitting with upper opening 411 of test specimen 410 and is received along axis A of measuring device 400 into test specimen 410 in order to pressurize sample 414 in cavity 412 of test specimen 410. Plunger 420 is coupled via rod 422 with pneumatic motor 421. The drive pressure of pneumatic motor 421 is a measure of the pressure P, exerted by plunger 420 on sample 414. Due to the form fit and the surface equality of plunger 420 and opening 411 of test specimen 410, the pressure P is in turn a direct measure for the force acting on sample 414. In a typical measurement, a start pressure, for example 0 bar, is acted upon, which is increased at appropriate intervals, for example 100 mbar, up to an end pressure, for example 5 or 6 bar. The pressure P is registered as a function of the time.

Figure 7:
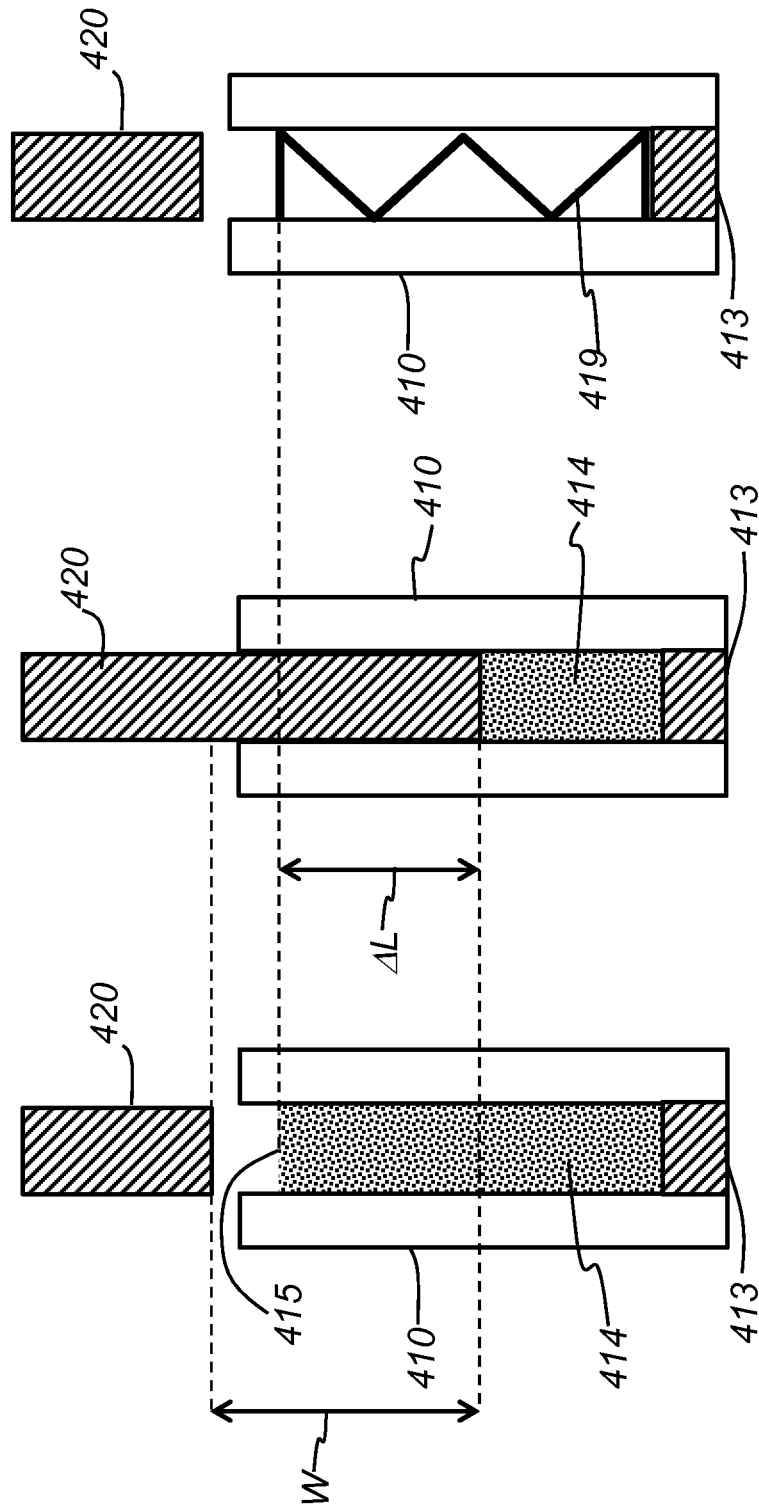
FIG. 7A shows a sample of a material filled in a test specimen before pressurization by the plunger.
FIG. 7B shows a sample of a material with filled in a test specimen after pressurization by the plunger.
FIG. 7C a test specimen filled with a calibration device.

Another one of measuring devices A1, . . . , Au is distance meter 440 for detecting distance W traveled by plunger 420 along axis A. For example, for this purpose, an inductive odometer that detects distance W, rod 422 travels relative to frame 403, which rigidly supports pneumatic motor 421 and test specimen holder 418. Consequently, this distance W (shown in FIG. 6) corresponds to the distance W of plunger 420 along axis A (as is shown in FIG. 7). Distance W is detected during the pressurization of plunger 420 as a function of time.

Another one of measuring devices A1 , . . . , Au is electrical measuring instrument 450. Plunger 420 is electrically conductive. If plunger 420 is in contact with sample 414, a current path forms along axis A of plunger 420 through sample 414 into the electrically conductive shutter 413 of test specimen 410. At plunger 420 and closure 413 is electrical measuring instrument 450 is connected in order to measure the end-to-end resistance R relative to the longitudinal axis A with a 2-point measurement configuration or, preferably, a current less 4-point measurement configuration, as illustrated in FIG. 6. Beneath closure 413 electrical contact 417.

Also conceivable is the measurement of an end-to-end resistance R with respect to longitudinal axis A or the additional determination of the temperature T of the sample by one or more thermometers 480, which for example is designed as a Peltier element. Thereby, the temperature change of sample 414, caused by compression, is detected at different locations of sample 414, which allows conclusions to be drawn about the heat capacity and thermal conductivity of material $M_j$. Electrical measuring instrument 450 includes, for example, voltage source 451 and ohm meter 452, preferably with plural series resistors (not shown) and a relay (not shown) in order to wire series resistors for preferably automated switching between different measurement ranges for high impedance and low impedance samples. The end-to-end resistance of sample 414 is detected during pressurization of plunger 420 as a function of time. An initially high impedance powder can become successively low impedance during pressurization, so it is convenient if the measuring range can be changed one or more times during a typical measurement.

Another one of the measuring devices A1, ..., Au is optical measurement instrument 460. Optical measurement instrument 460 can be a CCD camera. Likewise, the CCD camera can be equipped with a lighting device, in order to obtain an image of a portion of surface 415 of sample 414 under environmentally independent illumination conditions. It is also conceivable to arrange a calibration sample (not shown) in the optical path between sample 414 and the camera. The calibration sample may comprise a hole through which surface 415 is photographed, as well a color calibration mark, of at least three color segments spanning a color space (for example RGB), a white mark for calibrating the illumination conditions and the brightness distribution and/or a black and white mark for focusing the camera and for calibration of the edge sharpness or the contrast. The calibrations can be carried out computerized prior each measurement. The optical image of sample 414 can be captured during the pressurization of plunger 420 as a function of time. Alternatively, it is recorded only once or several times, preferably at defined time intervals, for example, when sample 414 is subjected to the initial pressure and the final pressure because then the principle pressure-induced morphology of the powder in sample 414 is in a defined and reproducible state. The optical measurement can be done along each spectral range, for example via the visual spectral range, an infrared spectral range, particularly for temperature detection, or a X-ray spectral range, for detecting structures of sample 414 below its surface 415. In particular, optical measuring instrument 460 may be mounted in test specimen holder 418 and directed to test specimen 410. Test specimen 410 is then made at least in part of the surface and/or transparent in the spectral regions to be measured.

Another of the measuring units A1, ..., Au may be an active or passive acoustic measuring instrument 470 for detecting the acoustic eigenspectrum of sample 414. In particular, acoustic measuring instrument 470 may be held in test specimen holder 418 and directed to test specimen 410 and is acoustically coupled with the powder via the test specimen 410. For this, test specimen 410 is formed such that it is resonant in the acoustic frequency ranges to be measured. Acoustic measuring instruments 470 can provide information about conditions of still or moving liquids, powders or solids, for example the filling level in test specimen 410, flow velocity of the powder or the presence or absence of impurities or foreign bodies. Acoustic transducer can generate electronic signals from acoustic oscillations.

In passive acoustic sensors, a noise that the observed process itself generates (for example the noise of the powder during the compression by plunger 420) is evaluated. Active acoustic sensors, for example, generate an ultrasonic field in order to excite the powder and to measure its sound frequency and/or time-resolved response. From these sound reflections, for example positions of boundaries can be determined by sound diffraction at edges or frequency changes (for example by means of the acoustic Doppler effect) velocities are determined.

Measurements with acoustic sensors are (for most materials $M_j$) non-invasive, suitably gentle to the particular requirements of material $M_j$, and flexibly adapted, for example by modulation of the excitation sound frequency. Acoustic measuring instrument 470 may comprise, for example a piezoelectric actuator or sensor. Piezoelectric devices are robust, reliable, easy to use, compact configurable and flexible to use. A piezoelectric material converts applied electrical voltage into mechanical or acoustic oscillations (operated as actuator) or vice versa (sensor mode). A piezoelectric crystal and piezoelectric actuator respectively coupled acoustically to sample 414 can therefore absorb the mechanical vibrations and convert them directly into an electrical measurement signal. The frequency spectrum of this electric signal depends definitely from the frequency spectrum of the mechanical vibrations detected by the piezo. The information to be measured is extractable from the frequency spectrum, for example its amplitude spectrum and phase spectrum and consists for example of material $M_j$ typical resonant frequencies. Preferably, the acoustic measurements are recorded during the pressurization of plunger 420 as a function of time.

It is also conceivable that optical instruments 460, acoustic measuring instruments 470 and/or thermometers 480 are integrated in plunger 420 and/or shutter 413 of test specimen 410.

Measuring device 400 has data acquisition device 460 communicatively connected to measuring units A1, ..., Au via data lines 401, so that it can detect k time-dependent measurement values of actual signature 200*j*. In particular, data acquisition device 460 is designed for synchronized recording of these k time-dependent measurement values. In an example embodiment, data acquisition device 460 is an analog-digital converter which converts the measurement values output, usually analog measured, from measuring units A1, ..., Au values into digital values. By synchronizing the time t can act as a correlation value between measured values by different measuring units A1, ..., Au. For example, pressure gauge 430, the pressure P=P (t) and distance meter 440 measures distance W=W (t) synchronized with one another as a function of the time t, so that the pressure P and distance W, for example, are correlated to a measured curve P(W) as a function of pressure P and distance W.

The information content of the correlated measured curve P(W) is higher than that of temporally uncorrelated measured curves of the pressure P=P(t) and the distance W=W (t). The additional information content is simply determined by fitting of the measured curve, for example with a sigmoid function in the form of fit parameters. Analogously, higher dimensional measured curves can be created and determined, for example the pressure P=P (W, R, T) in dependence of distance W, the end-to-end resistance R and a temperature T of sample 414. Actual signatures 200*j* or extended target signatures 100*i* can comprise both temporally correlated and uncorrelated values. An example of a time uncorrelated value with the pressure P=P (W, R, T) are values which have been extracted from a single captured image of the sample 414.

In derived actual signatures 300j and derived target signatures 300i are contained additional "hidden" correlations, which are evaluated by an algorithm according to the invention. Data acquisition device 460 is linked via standardized interface 461, for example a USB port, with local computer 541. Local computer 541 can execute the temporal correlation of the time-dependent measurement values P =P (t), W =W (t), R =R (t), etc., determine the fit parameters of correlated waveforms such as P(W), compile actual signatures 200i, determine derived actual signatures 300j by applying correlation 220i of target materials $M_1$ to actual signatures 200j and possibly perform the algorithm for determining selections 210i, correlations 220i and derived target signatures 300i for target materials $M_i$.

FIGS. 7A and 7B show test specimen 410 with filled sample 414 of material $M_j$ before and after application of a pressure P by plunger 420. Plunger 420 pulls back distance W. On this path, plunger 420 compresses sample 414 by a compression distance ΔL. The beginning of the compression distance ΔL results, for example, from the closing of the circuit between conductive plunger 420 and sample 414, conductive shutter 413, possibly test specimen holder 418 and electrical measuring instrument 450 or from the correlation of pressure P and distance W.

It is also conceivable that measuring device 400 is regularly calibrated with calibration device 419. Calibration device 419 is used, for example, for calibration of the measurements of pressure P, distance W and possibly resistance R and, for example, a conductive spring with defined electrical resistance and defined spring constant (both uncompressed and/or charged with a certain pressure P). As shown in FIG. 7C, calibration device 419 is, analog to sample 414, enclosed in a form-fitting manner in test specimen 410 of measuring device 400 and measured. It is conceivable that user 511, 521, 531 of measuring device 400 regularly measures calibration device 419 instead of sample 414. Alternatively, calibration device 419 can be included in a second test specimen 410 in test specimen holder 418 of measuring device 400, so that calibration device 419 can be measured simultaneously with sample 414.

Figure 8:
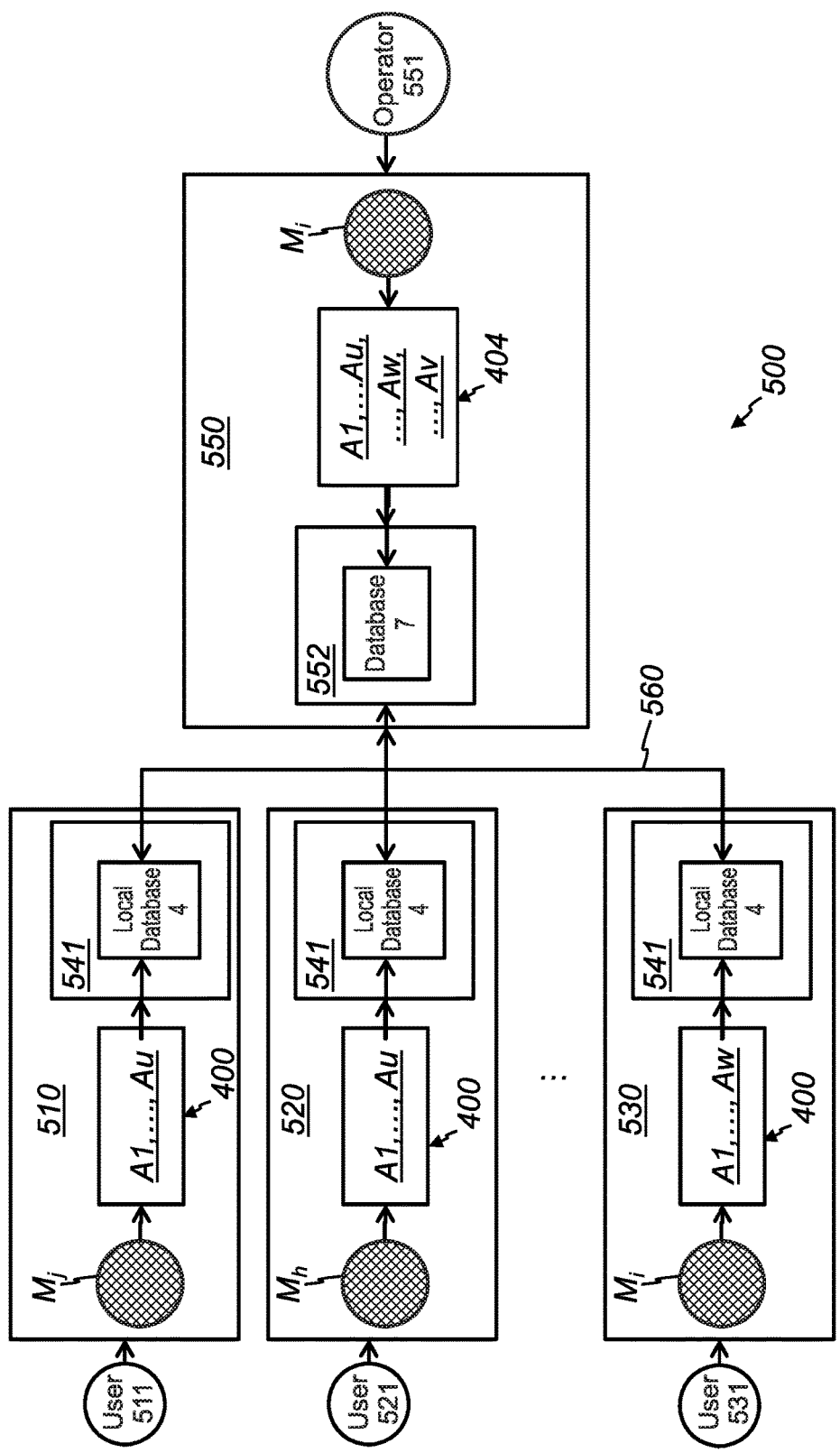
FIG. 8 is a schematic representation of a system according to the invention for identifying or distinguishing of materials.

FIG. 8 shows an exemplary embodiment of system 500 according to the invention for identifying or distinguishing of materials $M_j$ in a schematic representation. System 500 consists of at least one local unit 510, 520, 530, which is associated with a respective user 511, 521, 531. Furthermore, center 550 of operator 551 is at least associated with system 500.

Each local unit 510, 520, 530 includes at least one measuring device 400 for detecting at least one respective actual signature 220j for materials $M_j$. A preferred embodiment of such a measuring apparatus 400 is described with reference to the preceding FIGS. 6 through 7C. Measuring device 400 is communicatively coupled to local computer 541 of local units 510, 520, 530, respectively. Local computer 541 includes local database 4 and serves to store and/or process actual signature 220j.

According to the inventive concept, different types or classes of users 511, 521, 531 are integrated in system 500. A first class of users 511, 521, 531 uses their local unit 510, 520, 530 for quality control of materials $M_j$, $M_h$ like powders for plasma coating system or powdered food. They are interested in a fast, accompanying production, cost-effective, reliable, documentable and possibly certifiable powder analysis. Accordingly, measuring devices 400 of this first class of users 511, 521, 531 include a selection of measuring units A1, . . . , Au from all measuring units A1, . . . , Au, . . . , Aw, . . . , Av which can be used effectively for the analysis on materials $M_j$, $M_h$. Which u concrete measuring devices A1, . . . , Au, depends on the application and the technical specifications of user 511, 521, 531. These specifications are transmitted in the form of metadata to center 550 and are evaluated there, where they are considered in combination 40 of optimization criteria 41a, . . . 41p and their weighting 42a, . . . , 42p. For example, the color composition of a powdered dye for an auto paint shop is high and is low weighted for the manufacturer of non-visible primary color in the final product.

A second class of users are for example, analysis provider or university laboratories with measuring devices 400, which have a set w of measuring units A1, . . . , Aw. The w measuring devices A1, . . . , Aw can have u measuring devices A1, . . . , Au above the first class of users 511, 521, 531 or additional measuring devices that can collect meaningful measurements in time-intensive and/or cost-intensive manner, for example a synchrotron or elaborate (wet) chemical processes. This second class of users 511, 521, 531 can verify actual signatures 200j, collect additional measurement values if the identification or discrimination of material $M_j$, $M_h$ is not definite enough, or record extended target signatures 100i for target materials $M_i$, which are not yet stored in central database 7. Furthermore, they may transmit test conditions, test certificates as metadata. Also, users 511, 521, 531 of the first class can mutually check the measurements contained in actual signatures 200j. This "peer review" can be arranged through center 550 and advantageously be anonymous among users 511, 521, 531.

The at least one central 550 includes server 552 with central database 7 for storing and/or processing of actual signatures 220j of local units 510, 520, 530. Also in center 550, one or more further measuring devices 404 may be provided, which all A1, . . . , Au, . . . , Aw, . . . , Av, are useful dedicated to the analysis to each for user 511, 521, 531 relevant material. Materials $M_j$, $M_h$ are considered to be relevant if they are intended for the processing or use, or impurities or toxins that are excluded during processing or use.

Network 560 communicatively connects local computers 541 of local units 510, 520, 530 and the server. This communication link can exist in particular via the internet or an intranet of a company. This "cloud-based" system 500 enables the exchange of information among users 511, 521, 531. Preferably, local computers 541 are connected via server 552 of center 550, so that all actual signatures 200j of materials $M_j$, and (optionally) extended target signatures 100i of material $M_j$, are collected by users 511, 521, 531 in central database 7 and are able to be analyzed with server 552, for example in the manner as described with reference to FIGS. 1 to 4.

The maintenance and the training of central database 7 steadily improves the data situation about target material $M_i$, and thus identifying or distinguishing materials $M_j$, $M_h$ becomes more selective. At the same time, identifying or distinguishing becomes more efficient, because the sufficient accuracy for a particular user 511, 521, 531 requires, due to the improved data situation in central database 7, fewer measuring units A1, . . . , Au and measurement methods S1, . . . , Sl in measuring device 400 of local units 510, 520, 530.

An algorithm determines which measuring units A1, . . . , Au are dispensable. In the clustered recording and evaluation of the information of the whole system 500 on server 552 of center 550, an additional benefit exists for users 511, 521, 531 of local units 510, 520, 530. The additional benefit consists particularly in a statistically broader database of the collective of users 511, 521, 531 participating in system 500.

The basic idea of the invention is to improve the identifying or distinguishing of complex materials $M_j$ by a network-based analysis method and a good statistical basis, without the requirement of an analytical understanding of possibly highly complex composite material $M_j$. Another benefit is that each user 511, 521, 531 can also rely on the heuristic experience of other users 511, 521, 531. This is accessed indirectly via operator 551 of center 550 of system 500. Actual signatures 200j and metadata, provided by users 511, 521, 531 are in principle sensitive, because they allow to draw conclusions to trade secrets and production secrets. The anonymized grouping of these data with respect of third parties by a trusted operator 551 of center 550 allows all users 511, 521, 531 to benefit from the entire contents of central database 7, without revealing sensitive information. It is also conceivable that users 511, 521, 531 themselves maintain and train their local databases 4.

Figure 9:
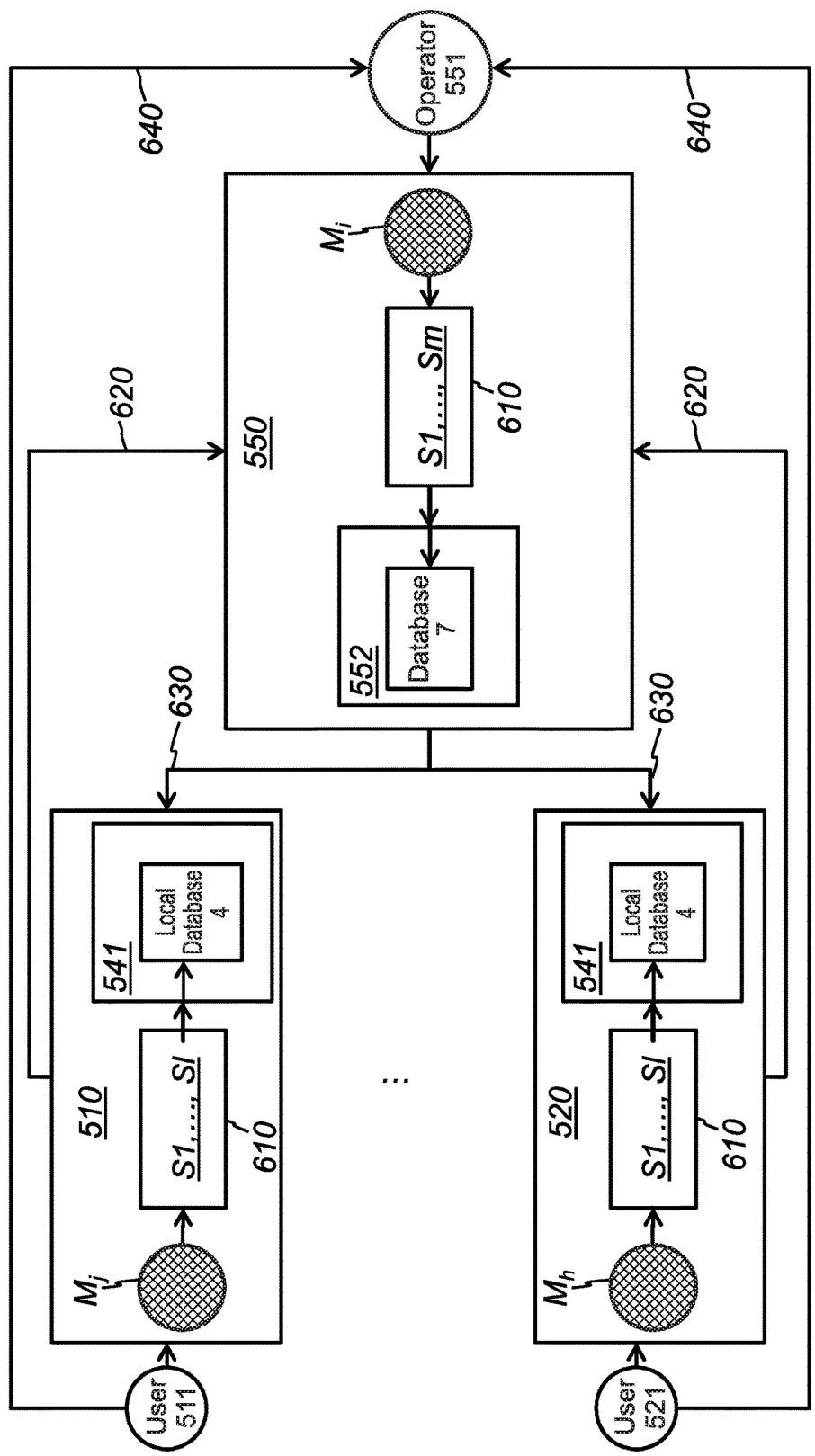
FIG. 9 is a schematic representation of the method for operating a system according to the invention for the identifying or distinguishing of materials.

FIG. 9 shows a schematic representation of the method for operating system 500 for identifying or distinguishing of materials $M_j$, in particular of system 500 as illustrated in FIG. 8.

In a first step of the process, acquiring 610 takes place of actual signature 220j of k different measured values of specific material $M_j$ by at least one user 511, 521, 531 of local unit 510, 520, 530 of system 500. The k various measurement values are collected with I different measurement methods S1, ..., Sl with u measuring units and A1, ..., Au. The I is greater than or equal to u because a measurement method S1, ..., Sl can collect only one or more measurement values, and likewise measuring unit A1, ..., Au only performs one or several measurement methods S1, ..., Sl. The same is true for n different measurement values, which are detected by the m different measurement methods S1, ..., Sk, ..., Sm by means of v measuring units A1, ..., Av. It follows that k, l, and u are less or equal to n, m, and v, respectively.

Acquiring step 610 is followed by requesting 620 of the at least one user 511, 521, 531 to operator 551 of center 550 of system 500. With the request, at least actual signature 220j is transmitted. In an example embodiment, metadata related to user 511, 521, 531 is transmitted with actual signature 220j. Metadata cover, for example, the identity of user 511, 521, 531, his specifications of material $M_j$, his comments or the device ID of its measuring units A1, ..., Au.

Forwarded by the at least one of the users, actual signatures 220j (and, when applicable, the metadata) are directly stored in non-volatile memory or buffered, evaluated and non-volatile stored in evaluated form on server 552 of center 550 of system 500. From actual signatures 220j (and, when applicable, from the metadata), derived target signature 300j is generated. As described with reference to FIGS. 1 to 3, this is done by applying correlation 220i per actual signature 220j for at least one target material $M_i$. Correlation 220i is based on extended signature 100i of target material $M_i$. Each of the extended signatures 100i consists of n different measurement values. On server 552 of center 550 of system 500, deviation δij is derived from actual signature 300j of material $M_j$, in relation to the respective extended signature 100i of the at least one target material $M_i$.

Then, reporting 630 is carried out by server 552 and operator 551 of center 550 of system 500, respectively, to the requesting user 511, 521, 531, if the respective deviation δij of material $M_j$ with respect to target material $M_i$ is less than tolerance Δ for target material $M_i$. In an example embodiment, this result can be returned as a list, which notes a probability in percent, which depends from the difference of deviation δij and tolerance Δ and, if applicable, taking the metadata into account with which material $M_j$ coincides with target material $M_i$. If the result is ambiguous because several target materials $M_i$ coincide with high probabilities with material $M_j$, there are two options that can take place in principle.

The first option includes the requesting user 511, 521, 531 evaluating the result and rejecting any implausible matches based on, for example, uncommunicated metadata or his experience. For example, a milk powder manufacturer would be able to reject a match of his milk powder with a powdery car paint, even if the metrological analysis indicates a high level of agreement. According to the invention, this evaluation 640 of the requesting user 511, 521, 531 is reported as feedback to operator 551 of system 500.

In the second option, the measured values of the actual signature 200j are collected by users 511, 521, 531 or operator 551 again, or are completed by additional readings of previously unrelated measurement methods S11 ..., Sm. In particular, evaluation 640 of requesting user 511, 521, 531 serves for further training of central database 7 and/or as a basis for decisions such as which measurement values need to be measured in addition, or whether a new target material $M_i$ needs to be defined. Also, empirical values can be saved as metadata and assigned to certain matches (for example, the above implausible coincidence between milk powder and car paint).

The entire invention is subject to the basic idea to improve the analysis of complex materials with networked and standardized measuring units and methods by recording and evaluating a wide statistical database without the need of an accurate analytical understanding of the interrelationships of various properties of complex materials. Therefore, features that apply with respect to one aspect of the invention, as defined in the independent claims, are also applicable to their other aspects. One skilled in the art will also understand that the disclosed features, removed from the context of illustrating the invention, merely have exemplary context, are combined with the features of the independent claims.

Although modifications and changes to the invention should be readily apparent to those having ordinary skill in the art, such modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention as claimed.

What is claimed is:

1. A method for identifying or discriminating materials with a system having at least one local unit, with each local unit having at least one measuring device for detecting at least one respective actual signature for the materials, the method comprising the steps of:
   acquiring the actual signature among a first quantity k of different measured values of a to be determined material by at least one user of a local unit of the system;
   providing a request of the at least one user to an operator of a center of the system, wherein with the request is the actual signature transmitted;
   storing the actual signature, provided by the at least one user, in non-volatile memory on a server of the center;
   creating a derived target signature from each of a plurality of correlations of at least one target material to the actual signature, wherein the plurality of correlations relate to an extended signature of the target material and wherein the extended signature consists of a second quantity n of different measured values and the second quantity n is greater than or equal to the first quantity k;
   calculating a deviation of each of the actual signatures for the material from the derived target signature for the at least one target material; and, reporting to the requesting user, for which target materials the respective deviation of the to be determined material, based on the at least one target material, is less than one for a target material defined tolerance.

2. The method of claim 1, wherein the actual signature is completed by metadata of the at least one user and/or to the operator.

3. The method of claim 2, wherein the metadata comprises a test report of at least the respective deviation and/or a certificate of the quality of the material and/or the measured actual signatures.

4. The method of claim 2, wherein for each user for at least one target material, the associated correlation and the associated derived target signature are optimized according to a combination of optimization criteria with associated weights, wherein the weights are modified based on metadata.

5. The method of claim 2, wherein the at least one user evaluates on the reporting of the operator the correct identification or discrimination of the material and reports a result of an evaluation back as metadata to the operator.

6. The method of claim 5, wherein the operator and/or a user on the basis of the metadata and/or the actual signatures:
extends the actual signatures with measurement values detected by additional measurement methods and optimizes the derived target signatures and correlations for at least one target material; or,
stores the to be determined material in a local database and/or in a central database as a new target material.

7. A method for identifying or discriminating of materials, comprising the steps of:
selecting I measurement methods from m different measurement methods, wherein the number I is less or equal to m measurement methods;
measuring an actual signature of a material by means of a measuring device for executing the I different measurement methods;
generating a derived actual signature for each measured actual signature of the material from at least one associated correlation of at least one target material to the actual signature;
determining a deviation per derived actual signatures of the material of a respective derived target signature of the at least one target material;
comparing each deviation with a tolerance specified for the respective target material; and
outputting for which target materials the respective deviation between the target material and material is less than the tolerance of the respective target material.

8. The method of claim 7, wherein the correlation associated with a target material enables the generation of the derived target signature from a target signature, wherein the target signature is generated by the selection from an extended signature.

9. The method of claim 8, wherein the actual signatures and the extended signatures consist of k and n measured values respectively, wherein the number n is greater than or equal to the number k.

10. The method of claim 9, wherein a target database for non-volatile storing of target data sets comprising the derived target signatures, the selections and the correlations for the at least one target material, is generated with the steps:

applying of the I different measurement methods for generating a respective extended signature of the at least n measured values for at least one target material;
creating a measurement database of extended signatures;
optimizing each of a derived target signature, which is generated by the associated correlation from the associated target signature, which is generated by a selection of the measuring methods;
applying of the n different measurement methods for generating a respective extended signature from the at least n measured values for at least one target material, which is suitable for product processing;
creating a database of extended signatures;
optimizing a derived target signature, which is generated by an associated correlation from an associated target signature, which is generated by a selection from the measurement methods; and,
creating the target database from the derived target signatures, the selections and correlations.

11. The method of claim 10, wherein a computer-based algorithm carries out the optimizing step.

12. The method of claim 10, wherein the optimizing step takes place after a combination of optimization criteria, which are provided with associated weights according to their relevance for the processing of a material in a device for product processing.

13. The method of claim 7, wherein in a database a selected subset of reference data sets is stored non-volatile, wherein the reference data each consist of selection of measurement methods, a target signature, the correlation and/or the derived target signature of at least one target material, and/or wherein in the database, audit records are logged, which consist of the actual signatures, the derived actual signatures and/or the deviations.

14. The method of claim 13, wherein audit records of the database are transmitted automatically via a digital network to a further external database.

15. The method of claim 14, wherein the audit records are used in the database as a control parameter for a control circuit in the processing in a device for product processing.

16. The method of claim 13, wherein an external storage medium, in which the nominal data sets and/or audit records are stored, is readable connected with a container, a packaging and/or a charge of a desired target material, or of a material.

17. The method of claim 16, wherein the external storage medium is made up of a Radio-Frequency Identification (RFID) chip is, on which the data sets are stored in the form of RFID tags and/or wherein the storage medium is made up of a label on which the data sets are stored alphanumeric and/or as a barcode.

18. The method of claim 7, wherein a suitability of the at least one material for processing in a device for product processing is checked during the ongoing production process.

19. The method of claim 7, wherein application of a selection of the I measurement methods is at least ten times faster than the application of m measurement methods.

20. The method of claim 7, wherein a data processing means reads a database and controls a reduced set of u measuring devices for performing the selection of measurement methods on a material such that values contained in a database, which are to be measured for the comparison of the material with several target material are not redundantly collected.

* * * * *